(12) United States Patent
Yin

(10) Patent No.: US 9,572,344 B2
(45) Date of Patent: Feb. 21, 2017

(54) GLUTARALDEHYDE BASED BIOCIDAL COMPOSITIONS AND METHODS OF USE

(71) Applicant: Dow Global Technologies LLC, Midland, MI (US)

(72) Inventor: Bei Yin, Buffalo Grove, IL (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/506,153

(22) Filed: Oct. 3, 2014

(65) Prior Publication Data
US 2015/0025079 A1 Jan. 22, 2015

Related U.S. Application Data

(62) Division of application No. 12/785,075, filed on May 21, 2010, now Pat. No. 8,889,679.

(60) Provisional application No. 61/180,941, filed on May 26, 2009.

(51) Int. Cl.
| | | |
|---|---|---|
| *A01N 35/04* | (2006.01) | |
| *A01N 43/64* | (2006.01) | |
| *A01N 35/02* | (2006.01) | |
| *A01N 43/90* | (2006.01) | |
| *C02F 1/50* | (2006.01) | |
| *C02F 103/00* | (2006.01) | |
| *C02F 103/02* | (2006.01) | |
| *C02F 103/10* | (2006.01) | |
| *C02F 103/14* | (2006.01) | |
| *C02F 103/30* | (2006.01) | |

(52) U.S. Cl.
CPC .............. *A01N 43/90* (2013.01); *A01N 35/02* (2013.01); *A01N 35/04* (2013.01); *A01N 43/64* (2013.01); *C02F 1/50* (2013.01); *C02F 2103/008* (2013.01); *C02F 2103/02* (2013.01); *C02F 2103/10* (2013.01); *C02F 2103/14* (2013.01); *C02F 2103/30* (2013.01)

(58) Field of Classification Search
None
See application file for complete search history.

(56) References Cited

U.S. PATENT DOCUMENTS

| | | |
|---|---|---|
| 4,048,336 A | 9/1977 | Winicov et al. |
| 4,093,744 A | 6/1978 | Winicov et al. |
| 6,177,070 B1 | 1/2001 | Lynch |
| 2008/0004189 A1 | 1/2008 | Smith et al. |

FOREIGN PATENT DOCUMENTS

| | | | |
|---|---|---|---|
| EP | 0439130 A1 | | 7/1991 |
| WO | WO 2009/158577 | * | 12/2009 |
| WO | WO 2010/108324 | * | 9/2010 |

OTHER PUBLICATIONS

Database WPI, Week 201120, Thomas Scientific, London, GB XP002718780 (2010).
"Product Information: Tris Nitro (Brand of Tris (Hydroxymethyl) Nitromethane)", XP55019278, pp. 1-9 (2002).
Sondossi, et al., "The effect of fifteen biocides on formaldehyde-resistant strains of Pseudomonas aeruginosa", J. Indus. Micro, vol. 1, No. 2, pp. 87-96 XP009170973 (1986).
Groot, et al., "Formaldehyde-releasers: relationship to formaldehyde contact allergy. Contact allergy to formaldehyde and inventory of formaldehyde-releasers", Contact Dermatitis, vol. 61, pp. 63-85 XP007914698 (2009).
Ferguson, "Data Evaluation Record Grotan", pp. 1-4 XP055096846 (2008).

* cited by examiner

*Primary Examiner* — Anna Pagonakis
(74) *Attorney, Agent, or Firm* — Tifani M. Edwards

(57) ABSTRACT

Provided are biocidal compositions comprising glutaraldehyde and a compound selected from the group consisting of 1-(3-chloroallyl)-3,5,7-triaza-1-azoniaadamantane; tris(hydroxymethyl)-nitromethane; and a hexahydrotriazine compound. The compositions are useful for controlling microorganisms in aqueous or water-containing systems.

1 Claim, No Drawings

GLUTARALDEHYDE BASED BIOCIDAL COMPOSITIONS AND METHODS OF USE

FIELD OF THE INVENTION

The invention relates to biocidal compositions and methods of their use for the control of microorganisms in aqueous and water-containing systems. The compositions comprise glutaraldehyde together with a second biocide.

BACKGROUND OF THE INVENTION

Protecting water-containing systems from microbial contamination is critical to the success of many industrial production processes, especially oil or natural gas production operations. In oil and gas operations, microorganism contamination from both aerobic and anaerobic bacteria can cause serious problems such as reservoir souring (mainly caused by anaerobic sulfate-reducing bacteria (SRB)), microbiologically influenced corrosion (MIC) on metal surfaces of equipment and pipelines, and degradation of polymer additives.

Microbial contamination can occur anywhere throughout oil and gas operations including injection water, produced water, downhole, near wellbore areas, deaeration towers, transmission pipelines, source water for waterflooding and hydraulic fracturing such as pond water and holding tank water, oil and gas storage tanks, and functional water-based fluids such as drilling muds, completion or workover fluids, hydrotest fluids, stimulation fluids, packer fluids, and fracturing fluids.

Biocides are commonly used to disinfect and control the growth of microorganisms in aqueous systems such as those found in oil and gas applications. However, not all biocides are effective against a wide range of microorganisms and/or temperatures, and some are incompatible with other chemical treatment additives. In addition, some biocides do not provide microbial control over long enough time periods. In oil and gas applications, the presence of $H_2S$ and high temperature (up to 120° C. or higher) present significant and unique challenges for biocide treatments.

Glutaraldehyde is an effective fast-acting biocide and is widely used in oil and gas applications. However, it is not stable under certain conditions such as high temperature (e.g. 80° C. and above) and, therefore, cannot provide long term microbial control in a downhole environment for example. It would be a significant advance in the art to provide thermally stable, fast acting, and long lasting biocides for oil and gas applications, including for downhole treatment where anaerobic SRB control is critical.

BRIEF SUMMARY OF THE INVENTION

In one aspect, the invention provides biocidal compositions. The compositions are useful for controlling microbial growth in aqueous or water-containing systems, and are particularly suited for applications in the oil and natural gas industry. The compositions of the invention comprise a synergistic combination composition comprising: glutaraldehyde; and 1-(3-chloroallyl)-3,5,7-triaza-1-azoniaadamantane wherein the synergistic weight ratio of glutaraldehyde; and 1-(3-chloroallyl)-3,5,7-triaza-1-azoniaadamantane ranges from 9:1 to 1:1.

In a second aspect, the invention provides a method for controlling microorganisms in aqueous or water-containing systems. The method comprises treating the system with an effective amount of a biocidal composition as described herein.

DETAILED DESCRIPTION OF THE INVENTION

As noted above, the invention provides biocidal compositions and methods of using them in the control of microorganisms. The compositions comprise glutaraldehyde together with a biocidal compound selected from the group consisting of: 1-(3-chloroallyl)-3,5,7-triaza-1-azoniaadamantane; tris(hydroxymethyl)-nitromethane; and a hexahydrotriazine compound. It has surprisingly been discovered that combinations of glutaraldehyde with other biocidal compounds as described herein are synergistic when used for microorganism control in aqueous or water-containing media. That is, the combined materials result in improved biocidal properties than would otherwise be expected based on their individual performance at the particular use-concentration. The observed synergy permits reduced amounts of the materials to be used to achieve acceptable biocidal properties, thus potentially reducing environmental impact and materials cost.

In addition to exhibiting synergy, the compositions of the invention are particularly effective at controlling anaerobic microorganisms. Further, the compositions are functional at both low and high temperature, and they also maintain their efficacy in systems that contain reducing agents, such as those that contain sulfide. As a result of these attributes, the compositions are particularly useful in the oil and natural gas industry where biocidal agents are needed that are capable of controlling microorganisms, including anaerobic microorganisms, over varying temperature ranges, and that continue to be effective even when reducing agents, such as sulfides, are present.

For the purposes of this specification, the meaning of "microorganism" includes, but is not limited to, bacteria, fungi, algae, and viruses. The words "control" and "controlling" should be broadly construed to include within their meaning, and without being limited thereto, inhibiting the growth or propagation of microorganisms, killing microorganisms, disinfection, and/or preservation against microorganism growth.

The present invention provides a synergistic combination composition comprising:
glutaraldehyde; and
1-(3-chloroallyl)-3,5,7-triaza-1-azoniaadamantane
wherein the synergistic weight ratio of glutaraldehyde; and 1-(3-chloroallyl)-3,5,7-triaza-1-azoniaadamantane ranges from 9:1 to 1:11.

Preferably, the glutaraldehyde to CTAC weight ratio in the first embodiment of the invention is about 100:1 to 1:100, more preferably 50:1 to 1:50, and even more preferably 20:1 to 1:20.

In a further preferred embodiment, particularly suited for use against anaerobic bacteria, the weight ratio of glutaraldehyde to CTAC is between about 9:1 to 1:11.

In a still further preferred embodiment, the microorganism is anaerobic and the aqueous system to be treated contains reducing agent, such as sulfide. Under this embodiment, the glutaraldehyde to CTAC weight ratio is preferably between about 2:1 to 1:11.

Glutaraldehyde and CTAC are commercially available from The Dow Chemical Company and/or can be readily prepared by those skilled in the art using well known techniques.

The compositions of the invention are useful for controlling microorganisms in aqueous or water-containing systems, such as those present in oil and natural gas applications. Examples of such systems include, but are not limited to, injection and produced water, source water for waterflooding and hydraulic fracturing such as pond water and holding tank water, functional fluids such as drilling muds, completion or workover fluids, hydrotest fluids, stimulation fluids, packer fluids, and fracturing fluids, oil and gas wells, separation, storage, and transportation systems, oil and gas pipelines, oil and gas vessels, or fuel.

The inventive compositions may also be used for controlling microorganisms in other industrial and water-containing systems such as cooling towers, heat exchangers, boiler systems, pulp and paper manufacture, other industrial process water, ballast water, wastewater treatment systems, reverse osmosis water processing, metalworking fluids, leather manufacture, paints and coatings, aqueous emulsions, latexes, adhesives, inks, pigment dispersions, personal care and household products, mineral slurries, caulks and adhesives, tape joint compounds, disinfectants, cleaners, textile fluids, or a system used therewith.

In addition, the blends may be employed in other areas where glutaraldehyde is used as a biocide and reduced loadings of gluataraldehyde are desired.

The compositions of the invention are suitable for use over a wide temperature range. In a preferred embodiment, the compositions are used in aqueous or water-containing systems at a temperature of 40° C. or greater. In further embodiments, the temperature of the aqueous or water containing system is 60° C. or greater, or is 80° C. or greater.

The compositions are also further effective when a reducing agent such as a source of sulfide ion is present in the aqueous or water-containing system.

The compositions are also additionally effective when a reducing agent such as a source of sulfide ion is present in the aqueous or water-containing system and the temperature of the aqueous or water containing system is elevated. Preferably, the temperature of the aqueous or water containing system in this embodiment is 40° C. or greater, or 60° C. or greater, or 80° C. or greater.

A person of ordinary skill in the art can readily determine, without undue experimentation, the concentration of the composition that should be used in any particular application. By way of illustration, a suitable actives concentration (total for both glutaraldehyde and the second biocide) is typically between 1 and 2500 ppm, preferably between 5 and 1000 ppm, based on the total weight of the aqueous or water-containing system including the biocides. In some embodiments for oil and gas applications, it is preferred that actives concentrations of the composition range from about 5 to about 500 ppm by weight, preferably about 10 to 300 ppm, for top side treatment, and from about 30 to about 1000 ppm, preferably about 50 to about 500 ppm, for downhole treatment.

The components of the inventive compositions can be added to the aqueous or water-containing system separately, or preblended prior to addition. A person of ordinary skill in the art can easily determine the appropriate method of addition. The composition can be used in the system with other additives such as, but not limited to, surfactants, ionic/nonionic polymers and scale and corrosion inhibitors, oxygen scavengers, and/or additional biocides.

"Alkyl," as used in this specification, encompasses straight and branched chain aliphatic groups. Preferred alkyl groups include, without limitation, methyl, ethyl, propyl, isopropyl, butyl, isobutyl, sec-butyl, tert-butyl, and pentyl.

By "hydroxyalkyl" is meant an alkyl group as defined herein above that is substituted with a hydroxyl group. Preferred hydroxyalkyl groups include, without limitation, hydroxymethyl and hydroxyethyl.

By "alkylene" is meant an alkyl group as defined herein above that is positioned between and serves to connect two other chemical groups. Preferred alkylene groups include, without limitation, methylene, ethylene, propylene, and butylene.

The following examples are illustrative of the invention but are not intended to limit its scope. Unless otherwise indicated, ratios, percentages, parts, and the like used herein are by weight.

EXAMPLES

The synergy indexes reported in the following examples are calculated using the following equation:

$$\text{Synergy Index} = Ca/CA + Cb/CB$$

where Ca: Concentration of biocide A required to achieve a certain level or complete bacterial kill when used in combination;

CA: Concentration of biocide A required to achieve a certain level or complete bacterial kill when used alone;

Cb: Concentration of biocide B required to achieve a certain level or complete bacterial kill when used in combination; and CB: Concentration of biocide B required to achieve a certain level or complete bacterial kill when used alone.

A synergy index (SI) of 1 indicates additivity, a synergy index of less than 1 indicates synergy, and a synergy index greater than 1 indicates antagonism.

Various methods known to those skilled in the art can be used for evaluating biocidal efficacy. In the examples below, aliquots of the biocide-treated samples are removed at predetermined time points and the biocide concentration required to achieve a certain level or complete bacterial kill is determined by culture-based methods including serial dilution. In some examples, the method is based or adapted (e.g., for high temperature testing or for the presence of sulfide) from the methodology described in international patent publication WO 2009/039004, which is incorporated herein by reference.

Example 1

Evaluation of glutaraldehyde/CTAC, glutaraldehyde/tris(hydroxymethyl)nitromethane (tris nitro), and glutaraldehyde/hexahydro-1,3,5-tris(2-hydroxyethyl)-s-triazine (HHT) Combinations against Anaerobic Bacteria Inside an anaerobic chamber, a deaerated sterile salt solution (3.1183 g of NaCl, 1.3082 mg of NaHCO3, 47.70 mg of KCl, 72.00 mg of CaCl2, 54.49 mg of MgSO4, 172.28 mg of Na2SO4, 43.92 mg of Na2CO3 in 1 L water) is contaminated with an oil field isolated anaerobic SRB consortium at final bacterial concentrations of $10^5$-$10^6$ CFU/mL. Aliquots of this contaminated water are then treated with biocide solution (single or in combination) at various concentrations. After the mixtures are incubated at 40° C. for 24 hour, the minimum biocide concentration to achieve complete bacteria kill (MBC) is determined. Table 1 summarizes the results for glutaraldehyde/CTAC combinations, Table 2 summarizes the results for glutaraldehyde/tris nitro, and Table 3 summarizes the results for glutaraldehyde/HHT combinations.

Biocidal efficacy of glutaraldehyde, CTAC, and glutaraldehyde/CTAC combinations against anaerobic bacteria.

| Ratio of Glutaraldehyde to CTAC | MBC (active ppm) | | Synergy Index |
|---|---|---|---|
| (active w/w) | Glutaraldehyde | CTAC | |
| 1:0 | 5.3 | 0.0 | |
| 9:1 | 5.2 | 0.6 | 0.98 |
| 3:1 | 3.4 | 1.1 | 0.64 |
| 1:1 | 3.1 | 3.1 | 0.61 |
| 1:3 | 3.8 | 11.3 | 0.80 |
| 1:9 | 3.6 | 32.3 | 0.92 |
| 0:1 | 0.0 | 133.3 | |

TABLE 2

Biocidal efficacy of glutaraldehyde, tris nitro, and glutaraldehyde/tris nitro combinations against anaerobic bacteria.

| Ratio of Glutaraldehyde to Tris Nitro | MBC (active ppm) | | Synergy Index |
|---|---|---|---|
| (active w/w) | Glutaraldehyde | Tris Nitro | |
| 1:0 | 4.0 | 0.0 | |
| 9:1 | 3.8 | 0.4 | 0.96 |
| 3:1 | 3.6 | 1.2 | 0.93 |
| 1:1 | 3.0 | 3.0 | 0.83 |
| 1:3 | 3.1 | 9.4 | 0.99 |
| 1:9 | 2.4 | 21.6 | 1.09 |
| 0:1 | 0.0 | 44.4 | |

TABLE 3

Biocidal efficacy of glutaraldehyde, HHT, and glutaraldehyde/HHT combinations against anaerobic bacteria.

| Ratio of Glutaraldehyde to HHT | MBC (active ppm) | | Synergy Index |
|---|---|---|---|
| (active w/w) | Glutaraldehyde | HHT | |
| 1:0 | 4.0 | 0.0 | |
| 9:1 | 3.9 | 0.4 | 0.97 |
| 3:1 | 3.8 | 1.3 | 0.95 |
| 1:1 | 3.4 | 3.4 | 0.89 |
| 1:3 | 2.7 | 8.2 | 0.74 |
| 1:9 | 2.5 | 22.7 | 0.80 |
| 0:1 | 0.0 | 133.3 | |

As shown in Tables 1-3, glutaraldehyde in combination with CTAC, tris nitro, or HHT exhibits a synergistic effect against anaerobic SRB at certain weight ratios. Lower dosages can therefore be used for good bacterial control when the biocides are used in combination instead of separately.

Example 2

Evaluation of glutaraldehyde/CTAC, glutaraldehyde/tris(hydroxymethyl)nitromethane (tris nitro), and glutaraldehyde/hexahydro-1,3,5-tris(2-hydroxyethyl)-s-triazine (HHT) Combinations against Anaerobic Bacteria for High Temperature and Sulfide-Rich Conditions Inside an anaerobic chamber, biocide solutions (single or in combination) are prepared at various concentrations in a salt solution (3.1183 g of NaCl, 1.3082 mg of NaHCO3, 47.70 mg of KCl, 72.00 mg of CaCl2, 54.49 mg of MgSO4, 172.28 mg of Na2SO4, 43.92 mg of Na2CO3 in 1 L water). The biocide solutions are challenged with $10^4$ to $10^5$ CFU/mL of an oil field isolated anaerobic SRB consortium and 10 ppm sulfide ion. The mixtures are incubated at 80° C. under anaerobic conditions for 2 hours after which the biocidal efficacy against the field SRB consortium is evaluated. The biocidal efficacy is determined by selecting the lowest biocide concentration required to achieve at least a 99.9% bacterial reduction in 2 hours. Synergy index is then calculated. Table 4 summarizes the results for glutaraldehyde/CTAC combinations, Table 5 summarizes the results for glutaraldehyde/tris nitro, and Table 6 summarizes the results for glutaraldehyde/HHT combinations.

TABLE 4

Biocidal efficacy of glutaraldehyde, CTAC, and glutaraldehyde/CTAC combinations against anaerobic bacteria for high temperature and sulfide-rich conditions.

| Ratio of Glutaraldehyde to CTAC | Dosage required for 99.9% bacterial kill in 2 h (active ppm) | | Synergy Index |
|---|---|---|---|
| (active w/w) | Glutaraldehyde | CTAC | |
| 1:0 | 8.7 | 0.0 | |
| 1.5:1 | 4.3 | 2.9 | 0.51 |
| 1:1.3 | 4.3 | 5.9 | 0.51 |
| 1:2.7 | 4.3 | 11.7 | 0.53 |
| 1:5.4 | 4.3 | 23.4 | 0.56 |
| 1:10.8 | 2.2 | 23.4 | 0.31 |
| 0:1 | 0.0 | 375.0 | |

TABLE 5

Biocidal efficacy of glutaraldehyde, tris nitro, and glutaraldehyde/tris nitro combinations against anaerobic bacteria for high temperature and sulfide-rich conditions.

| Ratio of Glutaraldehyde to Tris Nitro | Dosage required for 99.9% bacterial kill in 2 h (active ppm) | | Synergy Index |
|---|---|---|---|
| (active w/w) | Glutaraldehyde | Tris Nitro | |
| 1:0 | 22.5 | 0.0 | |
| 4:1 | 11.3 | 2.8 | 0.52 |
| 2:1 | 11.3 | 5.6 | 0.53 |
| 1:1 | 11.3 | 11.3 | 0.56 |
| 1:2 | 11.3 | 22.5 | 0.63 |
| 1:4 | 5.6 | 22.5 | 0.38 |
| 0:1 | 0.0 | 180.0 | |

TABLE 6

Biocidal efficacy of glutaraldehyde, HHT, and glutaraldehyde/HHT combinations against anaerobic bacteria for high temperature and sulfide-rich conditions.

| Ratio of Glutaraldehyde to HHT (active w/w) | Dosage required for 99% bacterial kill in 2 h (active ppm) | | Synergy Index |
|---|---|---|---|
| | Glutaraldehyde | HHT | |
| 1:0 | 15.6 | 0.0 | |
| 2:1 | 15.6 | 7.8 | 1.06 |
| 1:1 | 7.8 | 7.8 | 0.56 |
| 1:2 | 7.8 | 15.6 | 0.63 |
| 1:4 | 15.8 | 62.5 | 1.51 |
| 1:8 | 15.8 | 125.0 | 2.01 |
| 0:1 | 0.0 | 125.0 | |

As can be seen in Tables 4-6, glutaraldehyde in combination with CTAC, tris nitro, or HHT exhibits a synergistic effect against anaerobic SRB for high temperature and sulfide-rich conditions at certain weight ratios. Lower dosages can therefore be used for good bacterial control when the biocides are used in combination instead of separately.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A synergistic combination composition comprising:
   glutaraldehyde; and
   1-(3-chloroallyl)-3,5,7-triaza-1-azoniaadamantane
   wherein the synergistic weight ratio of glutaraldehyde; and 1-(3-chloroallyl)-3,5,7-triaza-1-azoniaadamantane ranges from 9:1 to 1:11.

* * * * *